United States Patent [19]

Raizon et al.

[11] Patent Number: 4,638,080
[45] Date of Patent: Jan. 20, 1987

[54] PREPARATION OF DIPHENYLAZOMETHINES

[75] Inventors: Bernard Raizon, Vigneux; Guy Rossey, Montigny-Le-Bretonneux; Alexander Wick, St Nom-De-Breteche, all of France

[73] Assignee: Synthelabo, Paris, France

[21] Appl. No.: 832,690

[22] Filed: Feb. 25, 1986

[30] Foreign Application Priority Data

Feb. 26, 1985 [FR] France ................ 85 02724

[51] Int. Cl.$^4$ .......................... C07C 101/72
[52] U.S. Cl. ................ 560/35; 562/440; 564/104; 564/181; 564/269
[58] Field of Search ............ 560/35; 562/440; 564/164, 181, 269

[56] References Cited

U.S. PATENT DOCUMENTS

| | | | |
|---|---|---|---|
| 4,094,992 | 6/1978 | Kaplan et al. | 562/440 |
| 4,400,394 | 8/1983 | Kaplan et al. | 560/35 |
| 4,478,851 | 10/1984 | Kaplan et al. | 562/269 |

FOREIGN PATENT DOCUMENTS

| | | | |
|---|---|---|---|
| 2634288 | 2/1977 | Fed. Rep. of Germany | 562/440 |
| 2131024 | 6/1984 | United Kingdom | 562/440 |

*Primary Examiner*—James H. Reamer

[57] ABSTRACT

Process for preparing diphenylazomethines of formula (II)

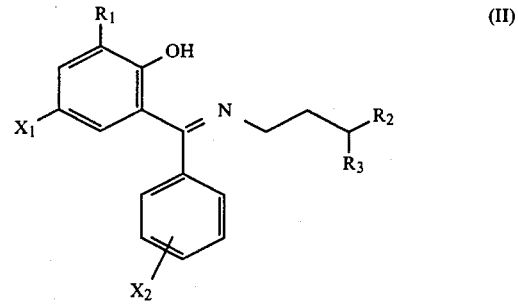

by decarboxylation of diphenylazomethines of formula (I)

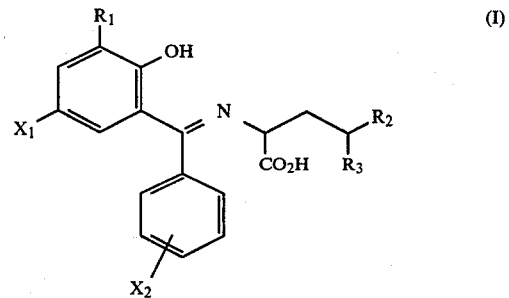

in which
$X_1$ and $X_2$ each denote, independently of each other, a hydrogen atom or a halogen atom or a methyl radical,
$R_1$ is H or linear or branched ($C_{1-4}$) alkyl radical,
$R_2$ is the radical COOH, a linear or branched ($C_{1-4}$) alkyl radical, the radical $CONH_2$ or a linear or branched $COO(C_{1-4})$ alkyl radical, and
$R_3$ denotes a hydrogen atom or the methyl radical.

2 Claims, No Drawings

PREPARATION OF DIPHENYLAZOMETHINES

The present invention relates to the preparation of diphenylazomethines which can be used in therapeutics and which have already been described by the Applicant in its French Pat. Nos. 75/24,065, 76/21/922, 80/03,009, 81/04,478, 81/21,559, 82/18,193, 82/18,194, 82/19,981 and 83/07,863.

The present invention provides compounds of formula (I)

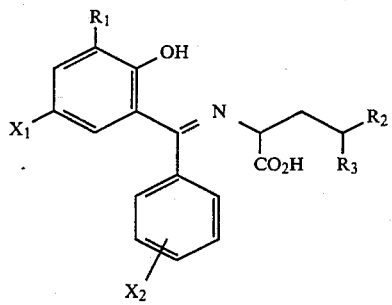

wherein $X_1$ and $X_2$ are the same or different and each is hydrogen, halogen or methyl; $R_1$ is hydrogen or straight or branched $(C_{1-4})$alkyl; $R_2$ is —COOH, straight or branched $(C_{1-4})$alkyl, —CONH$_2$ or straight or branched —COO$(C_{1-4})$alkyl and $R_3$ is hydrogen or methyl.

The compounds of formula (I) contain an asymmetric carbon atom and can exist in the form of racemates and of optically active isomers.

The compounds of formula (I) are prepared by reacting a benzophenone compound of formula (III)

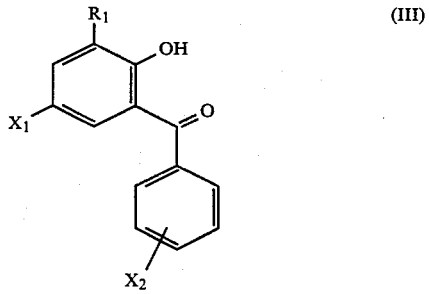

wherein $X_1$, $X_2$ and $R_1$ are as defined in relation to formula (I), with an amino acid of formula (IV)

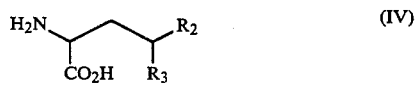

wherein $R_2$ and $R_3$ are as defined in relation to formula (I), in a solvent, in the presence of a base, at a temperature of from 60° to 80° C.

The compounds of formula (I) are useful as intermediates in the preparation of diphenylazomethines of formula (II)

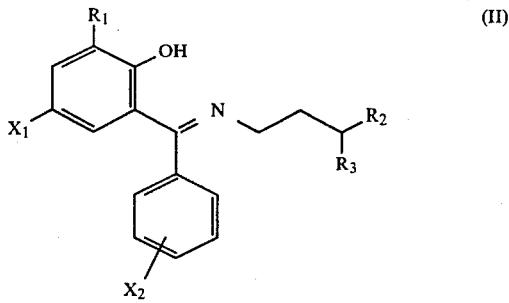

wherein $X_1$, $X_2$, $R_1$, $R_2$ and $R_3$ are as defined above in relation to compounds of formula (I) and in therapeutics, for example as antiepileptics, antidepressants and antidyskinetics.

The compounds of formula (II) may be prepared by decarboxylation of compounds of formula (I), for instance by heating under reflux in a solvent, such as toluene, for a time which can vary according to the starting materials, reaction conditions etc, with an excellent yield.

The following Examples are provided to illustrate the invention. The structures of the compounds have been confirmed by analyses and IR and NMR spectrometry.

EXAMPLE 1

(Preparation of 5-Amino-2-[((5-chloro-2-hydroxy-3-methylphenyl)(4-chlorophenyl)methylene)imino]-5-oxopentanoic acid (a compound of formula (I))

A mixture of 10 g (0.0355 mole) of (5-chloro-2-hydroxy-3-methylphenyl)(4-chlorophenyl)methanone, 5.2 g (0.0355 mole) of glutamine and 3 g (0.0355 mole) of sodium bicarbonate in 300 ml of methanol is evaporated to dryness under slightly reduced pressure (bath at 80° C.). The residue is then stirred at 80° C. under reduced pressure for 15 minutes. 300 ml of methanol are then added and evaporated off under the same conditions as previously. This operation is repeated 5 times. The final cooled residue is dissolved in 1.2 l of water and is acidified to pH 4, with stirring, by adding citric acid. It is extracted with chloroform, the organic phase is washed with water, separated, dried over MgSO$_4$, filtered, and evaporated to dryness. The solid obtained is transferred onto a sinter with 100 ml of pentane. It is filtered, drained and recrystallized twice from ethyl acetate with charcoal treatment. The crystals are filtered, drained, washed with the minimum quantity of ether, drained and dried in a heated desiccator at 60° C. The compound obtained melts at 177°–178° C.

EXAMPLE 2

(Preparation of 4-{[(5-Chloro-2-hydroxy-3-methylphenyl)(4-chlorophenyl)-methylene]imino}butanamide, (a compound of formula (II)).

A solution of 60 mg of the compound obtained in Example 1 in 7.5 ml of toluene is heated at reflux temperature for 15 minutes. The reaction mixture is evaporated to dryness and the residue is crystallized from 10 ml of ether. The crystals are filtered, drained and dried in a heat desiccator at 60° C. in the presence of P$_2$O$_5$. The product obtained melts at 154°–155° C.

The following table shows the compounds prepared in Examples 1 and 2 and further compounds of formula (I) and (II) prepared in similar manner.

TABLE

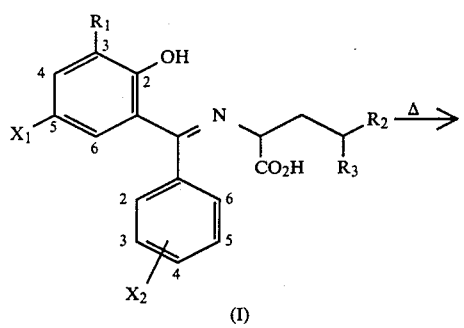

(I)

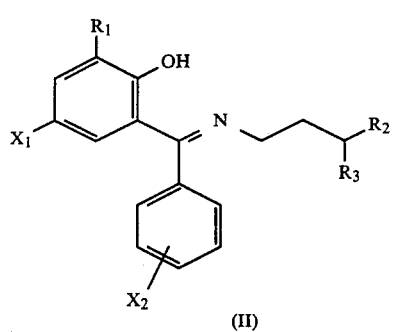

(II)

| Compound | $X_1$ | $X_2$ | $R_1$ | $R_2$ | $R_3$ | Compound I m.p. (°C.) | Compound II m.p. (°C.) |
|---|---|---|---|---|---|---|---|
| 1 | 5-Cl | 4-Cl | $CH_3$ | $CONH_2$ | H | 177–178 | 154–155 |
| 2 | 5-Cl | 4-Cl | $CH_3$ | COOH | H | 139–140 | 131–132 |
| 3 | 5-Cl | 4-Cl | $nC_3H_7$ | $CONH_2$ | H | 152–153 | 129–130 |
| 4 | F-5 | 4-Cl | H | $CONH_2$ | H | 126–127 | 143–144 |
| 5 | 5-Cl | 2-Cl | H | $CH_3$ | H | 165–166 | 54–55 |
| 6 | 5-Cl | 2-Cl | H | $iC_3H_7$ | $CH_3$ | 144–145 | 47–48 |

We claim:

1. A process for preparing a compound of formula (II)

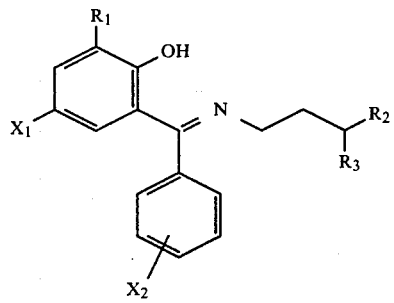

wherein $X_1$ and $X_2$ are the same or different and each is hydrogen, halogen or methyl; $R_1$ is hydrogen or straight or branched $(C_{1-4})$alkyl; $R_2$ is —COOH, straight or branched $(C_{1-4})$alkyl, —$CONH_2$ or straight or branched —$COO(C_{1-4})$alkyl and $R_3$ is hydrogen or methyl, comprising decarboxylating a compound of formula (I)

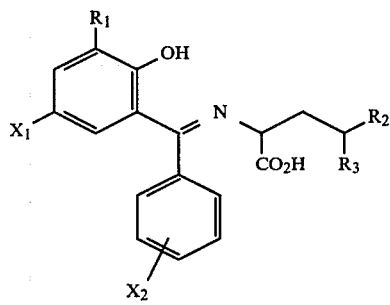

wherein $X_1$, $X_2$, $R_1$, $R_2$ and $R_3$ are as defined above.

2. Carboxylated diphenylazomethines, used for the preparation fo diphenylazomethines (II) as defined in claim 1, having the formula (I)

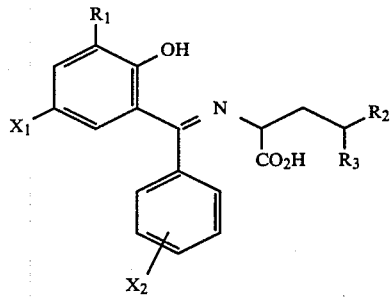

wherein $X_1$ and $X_2$ are the same or different and each is hydrogen, halogen or methyl; $R_1$ is hydrogen or straight or branched $(C_{1-4})$alkyl; $R_2$ is —COOH, straight or branched $(C_{1-4})$alkyl, —$CONH_2$ or straight or branched —$COO(C_{1-4})$alkyl and $R_3$ is hydrogen or methyl, with the exception of the compounds in which $X_1$=H, $CH_3$ or Cl, $X_2$=H, $R_1$=H, $R_2$=$CONH_2$, $R_3$=H and $X_1$=H, $CH_3$ or Cl, $X_2$=H, $R_1$=H, $R_2$=$R_3$=$CH_3$.

* * * * *